United States Patent [19]
Wortrich

[11] Patent Number: 5,464,421
[45] Date of Patent: Nov. 7, 1995

[54] HEMORRHAGE OCCLUDER, APPLICATOR AND METHOD

[75] Inventor: Theodore S. Wortrich, Long Beach, Calif.

[73] Assignee: Surgin Surgical Instrumentation, Inc., Tustin, Calif.

[21] Appl. No.: 373,523

[22] Filed: Jan. 17, 1995

Related U.S. Application Data

[63] Continuation of Ser. No. 96,650, Jul. 22, 1993, abandoned, which is a continuation of Ser. No. 715,492, Jun. 14, 1991, abandoned.

[51] Int. Cl.$^6$ .................................................. A61B 17/04
[52] U.S. Cl. ...................... 606/213; 606/139; 81/177.1; 81/177.6; 81/44
[58] Field of Search ..................... 606/139, 158, 606/213; 29/229, 243.56; 81/44, 53.2, 58.3, 177.1, 177.2, 489, 490

[56] References Cited

U.S. PATENT DOCUMENTS

| | | | |
|---|---|---|---|
| 2,372,930 | 4/1945 | Bovee | 81/177.6 |
| 2,483,379 | 9/1949 | Brell | 29/229 |
| 2,802,211 | 8/1957 | Friedman | 81/44 |
| 3,470,600 | 10/1969 | Hosbach | 29/229 |
| 4,631,985 | 12/1986 | Roberts | 81/44 |
| 4,712,550 | 12/1987 | Sinnett . | |
| 4,784,138 | 11/1988 | Sinnett . | |
| 4,895,148 | 1/1990 | Bays et al. . | |

FOREIGN PATENT DOCUMENTS

| | | | |
|---|---|---|---|
| 290135 | 11/1931 | Italy | 81/44 |
| 246326 | 9/1947 | Switzerland | 81/177.6 |

OTHER PUBLICATIONS

Irwin R. Berman, "Sutureless Laparoscopic Rectopexy For Procidentia," Dis Colon Rectum, Jul. 1992, pp. 689–693.
S. Nivatvongs, M.D. and D. T. Fang, M.D., "The Use of Thumbtacks to Stop Massive Presacral Hemorrhage", Dis. Col. & Rect. (Sep., 1986), pp. 589–590.
W. Qunyao, M.D., S. Weijin, M.D., Z. Youren, M.D., Z. Wenqing, M.D. and H. Zhengrui, "New Concepts in Severe Presacral Hemorrhage During Proctectomy", Arch. Surg (1985), vol. 120; pp. 1013–1020.

*Primary Examiner*—Gary Jackson
*Attorney, Agent, or Firm*—Merchant, Gould, Smith, Edell, Welter & Schmidt

[57] ABSTRACT

An occluder pin (10) has a cap (14) and shaft (16) with a plurality of serrations (18) disposed along the shaft (16). The serrations have a beveled trailing surface (20) which facilitates easy insertion of the pin in a substantially perpendicular leading surface which provides for resisting withdrawal of the pin (10). An applicator (12) has a handle (30) attached to a bendable shaft (28). A C-shaped yoke-type pin cap holder (32) includes a pair of flexible arms (34) which retain the pin cap (14) but flex out so that the pin (10) may be slid between the opening between the ends of the arms (34).

8 Claims, 4 Drawing Sheets

HEMORRHAGE OCCLUDER, APPLICATOR AND METHOD

This is a continuation, of application Ser. No. 08/096,650, filed Jul. 22, 1993, now abandoned, which is a continuation of application Ser. No. 07/715,492, filed Jun. 14, 1991, now abandoned.

BACKGROUND OF THE INVENTION

This invention relates to devices and methods for terminating hemorrhaging in colorectal surgery, and more particularly to devices and methods for terminating bleeding in the presacral venous plexus and the sacral basivertebral veins during surgery.

In colorectal surgery, certain incidents can give rise to massive bleeding that cannot conveniently be terminated by suturing or cauterizing. If the presacral fascia are inadvertently entered during rectal surgery, bleeding from the presacral venous plexus and the sacral basivertebral veins may occur. Due to the high density of blood vessels and high volume of blood flow in the region, inadvertent cuts result in severe blood loss which may lead to death in some cases. The urgency of the surgical procedure and the inaccessibility of the hemorrhaging site, as well as the severity of the bleeding, require that hemostatic measures of an unusual kind promptly be undertaken, as commonly used techniques such as packing the site or cauterizing the area often prove ineffective. It is known to terminate the bleeding by occluding or tamponading the vein, using a sterilized pin in the general form of a thumbtack and inserting it into the sacral vertebrae, in such a position that the pin itself or the head of the pin closes the vein. More than one bleeding site must often be occluded during these surgeries.

While this procedure has been used for a number of years, it is accompanied by a number of problems pertaining to uncertainties of inserting the occluder pin. Ideally the hemorrhage occluder pin should be inserted so that the head of the pin rests on the fascia or bone. However, because of the close confinement in the working area, it is not always possible to seat the head properly. Therefore it is important that the accidental dislodging of a partially inserted pin be as difficult as possible. This insures that the bleeding vessels will remain occluded during critical phases of healing and that an abnormal movement, jarring or trauma will not dislodge the hemorrhage occluder pin.

It is difficult in many instances to precisely position and insert the pin. The edges of the head of the pin are quite thin and the shaft of the pin is quite short, so that holding the pin with one's fingers is often difficult. The surgeon must use one hand to locate and control the bleeding while the other is used to handle the occluder. This often results in the pin being dropped and leads to chances of puncturing the surgeon's gloves and skin, exposing the surgeon to the risk of blood-transmitted diseases, such as hepatitis or acquired immune deficiency syndrome. In an improved, but not entirely satisfactory technique, the thumbtack is held at its shaft with a surgical clamp, and the surgeon positions and forces in the thumbtack before releasing the clamp. The typical clamp is cumbersome, obscures the surgeon's view and introduces some interference with the head or the shaft, or both, at the point of insertion. Moreover the straight length of the shaft may not permit convenient access to the bleeding site, or positioning in the proper relationship. Quick and certain application regardless of access problems cannot often be achieved by existing devices and procedures.

It can be seen then that an improved occluder pin is needed that is easily and precisely insertable into the sacral vertebrae but resists withdrawal. It can also be seen that improved application devices and methods of location and insertion are needed that position and securely hold the pin.

SUMMARY OF THE INVENTION

An occluder pin in accordance with the invention comprises a member having an integral head portion of circular outline, and an axial pin length of between 5 and 12 mm, the pin being integral with the head and including a number of circumferential serrations/grooves disposed along its length. In a particular example, the pin shaft has a diameter in the range of about 0.5 to 1.5 mm and a length of 5 to 12 mm, with a head having a diameter of 5 to 15 mm, the pin being of biologically inert material such as titanium. The pin shaft also has four equally spaced serrations with radial leading edges and beveled trailing edges at an angle of approximately 11°, providing maximum serration depths of about 0.2 mm. Occluder pins thus configured will more readily and firmly seat in the bony cortex and assure closure of vessels and cessation of blood flow.

A modified form of occluder pin incorporates a slightly tapered shaft having circumferential serrations which may be undercut slightly at the leading edge shoulder, while the superior surface of the cap has a central indentation for receiving an inserter device by which the surgeon may exert greater local force.

An applicator for aiding in inserting the pin comprises a handle with a malleable extender shaft, and a terminal pin holder at the opposite end from the handle. The holder has a pair of curved arms for receiving the periphery of the cap of the pin. The arms are of a material which will spread slightly under manual force to allow the cap of the pin to slide out from the holder in the direction parallel to the plane of the cap. In using the occluder pins and applicator, the surgeon manually conforms the handle and the malleable extender shaft to the shape needed to place the pin in perpendicular relation to the desired region of the sacral vertebrae, while remaining free of obstructions presented by tissues surrounding the bleeding site. The surgeon then positions the pin at that site, pressing the pin into the bony cortex with a finger of one hand via the cap and separating the applicator from the pin with the other hand. The forces involved are such that the extender shaft retains its shape while the pin is easily released.

A different applicator in accordance with the invention facilitates implantation of a number of pins during a given colorectal surgical procedure. The head of the applicator includes a storage channel for one or more pins, which can be fed along between side grooves to curved terminal areas where the pin to be used is retained. The storage channel is designed so that the caps of the pins are accessible but the pin points are not protruding, while the arms depend from the storage channel so that the pin may be pressed into position in like convenient fashion.

These and various other advantages and features of novelty which characterize the invention are pointed out with particularity in the claims annexed hereto and forming a part hereof. However, for a better understanding of the invention, its advantages, and the objects obtained by its use, reference should be made to the drawings which form a further part hereof, and to the accompanying descriptive matter, in which there is illustrated and described specific examples of devices and methods in accordance with the invention.

BRIEF DESCRIPTION OF THE INVENTION

In the drawings, wherein like reference numerals and letters indicate corresponding elements throughout the several views.

DETAILED DESCRIPTION OF THE INVENTION

Figure 1:
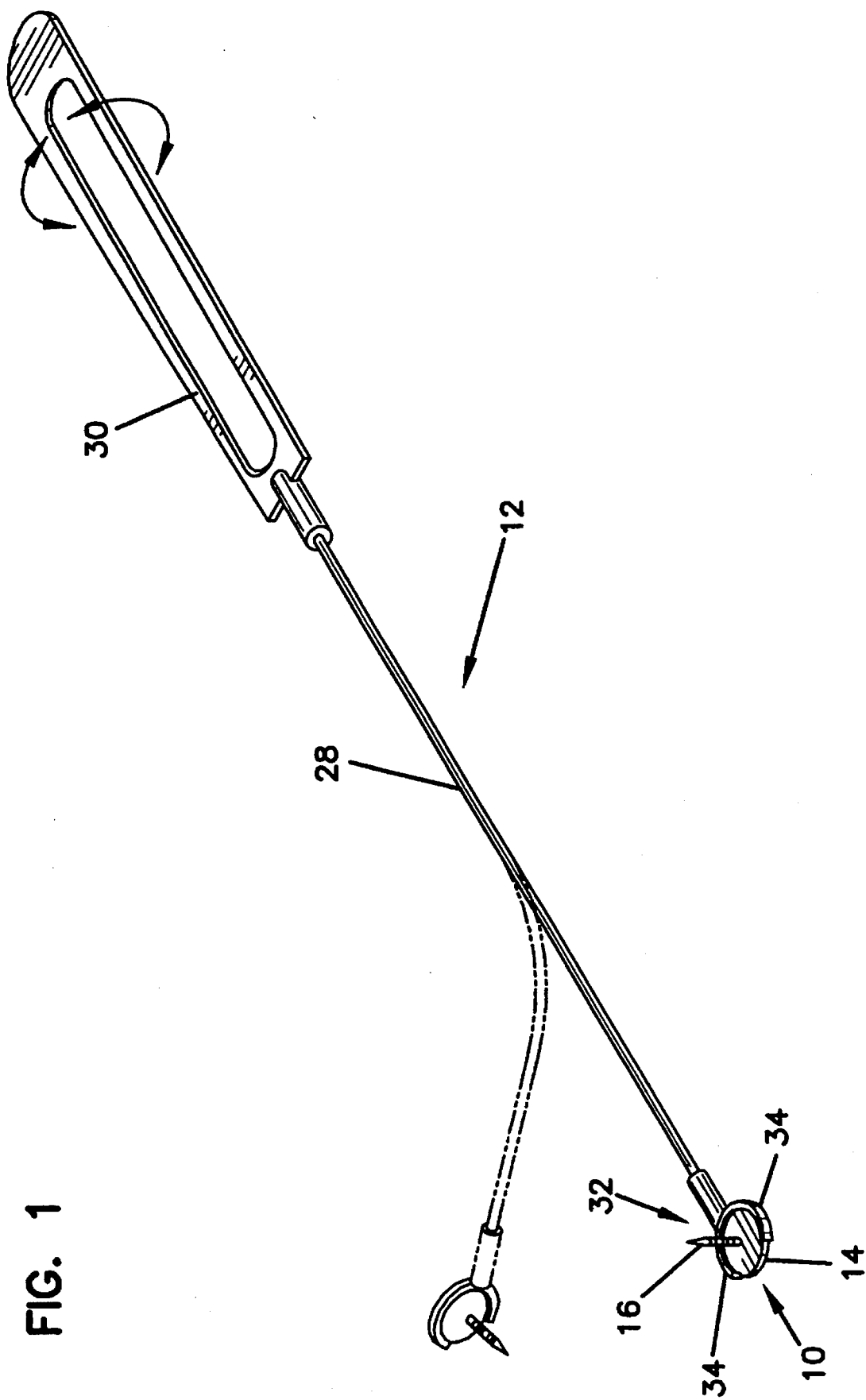
FIG. 1 shows a perspective view of an occluder pin and applicator and shows the extender shaft of the applicator bent in phantom according to the principles of the present invention.

Referring now to the drawings, there is shown in FIG. 1 an occluder pin 10 held by an applicator 12 in accordance with the invention. The pin 10 has a disk-shaped head or cap 14 with a pin shaft 16 extending axially from the center of the disk. The head or cap 14 of the pin 10 has a diameter of between 5 mm and 15 mm, (being 9.5 mm in this example) and a rim of 0.7 to 1.2 mm in height (1.0 mm in this example). The shaft 16 has a length in the range of 5 mm to 12 mm, specifically 7.5 mm in the exemplified version, and a diameter of about 0.5 mm to 1.5 mm, specifically 1.0 mm here.

Figure 2:
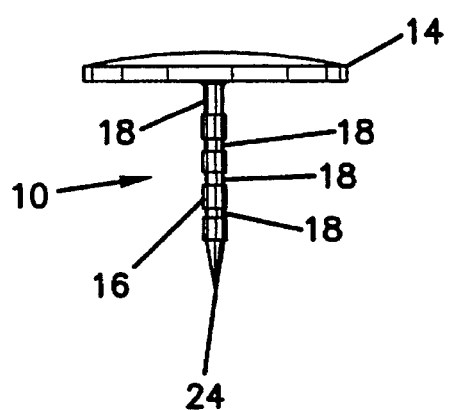
FIG. 2 is a side view of the occluder pin shown in FIG. 1.
Figure 3:
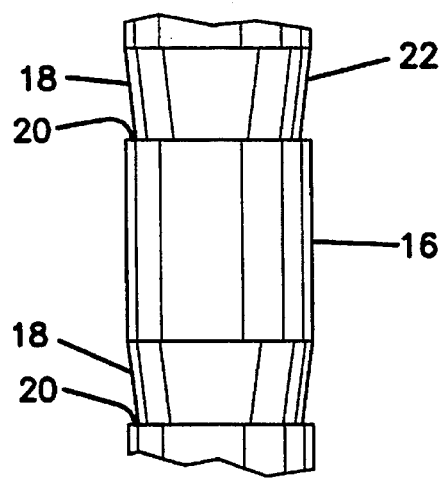
FIG. 3 is an enlarged view showing a detail of the serrations on the pin seen in FIG. 2.

As shown in FIGS. 2 and 3, disposed along the pin shaft 16 are a plurality of circumferential serrations 18 extending around the periphery of the pin shaft 16. In this example, four serrations 18 are spaced evenly along the length of the shaft 16. Each serration 18 has a beveled trailing surface 22 which tapers inward down in the direction toward a pointed tip 24 of the pin shaft 16. The beveled surface 22 meets a flat radial surface 20 at the leading edge that extends perpendicularly to the axis of the pin shaft 16 in the serration 18. In the preferred embodiment, the depth of the radial leading edge surfaces 20 of the circumferential serrations is between 0.1 mm and 0.3 mm, while the angle of the taper of surfaces 22 is approximately 11° and generally between 5° and 15°. The tapered trailing surfaces 22 of the serrations 18 facilitate easy insertion of the pin 10 into surrounding bony cortex. The leading edges 20 however catch the bony cortex around the shaft 16 upon attempted withdrawal of the pin 10 so that the edges 20 act as a slight barb and the pin 10 resists removal from the bony cortex while inserted. The leading edges 20 are not so deep, however, as to prevent removal of the pin 10 without undue laceration of the surrounding bony cortex and tissue after hemorrhaging has been fully stabilized, if removal is indicated.

In the depicted example, the pin 10 is made from biologically inert or inactive material that is non-reactive and therefore safe for use in the body. Titanium has been widely used in these applications, and is the preferred example here, but stainless steel, other metal alloys, and other sterilizable materials of suitable physical properties such as plastics may be employed if they can properly be sterilized. The pin 10 therefore may be left in place for extended periods of time to control hemorrhaging. In any event the pin and applicator are presterilized or placed in sterile condition prior to use.

Figure 5:
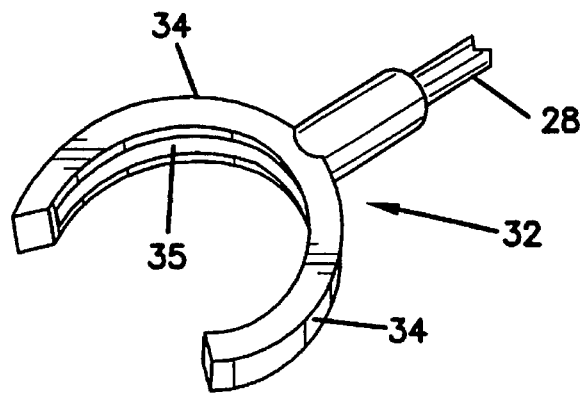
FIG. 5 is an enlarged perspective view of the pin holder showing the interior groove in the yoke structure.

As shown in FIG. 1, the applicator 12 has a flat handle 30 which is mounted on a first end of an extender shaft 28. The handle 30 is typically fixed to the extender shaft 28, but may also be rotatable against friction relative to the longitudinal axis of the shaft 28. Fixed attachment of handle 30 to shaft 28 is generally acceptable because twisting of the malleable shaft 28, together with some turning of the wrist by the surgeon will accommodate most changes that may be desirable. If the handle 30 is to be frictionally rotatable an indented or protruding element (not shown) of conventional type may be used to prevent possible separation of the handle 30 from the shaft 28. In either event, the handle may be turned to the most comfortable and easily-gripped position for a given access situation. The shaft 28 connects at its second end to a C-shaped yoke-type pin cap holder 32 of a material such as an industrial plastic. The holder 32 has arcuate arms 34 with an interior groove 35, as best seen in FIG. 5. The shaft 28 is malleable so that it may be bent to a variety of angles, one of which is shown in phantom. The shaft 28, however, lacks a memory characteristic and is sufficiently rigid, so that it will retain its shape conforming to the optimum insertion configuration for placing the pin 10. Control of the position of the handle 30 in combination with bending of the malleable extender shaft 28 enables the pin 10 to be positioned in a desired attitude by the surgeon at the bleeding site, while also enabling the surgeon to press in the pin itself.

The holder 32 is shaped so that the periphery of the pin cap 14 is retained within the arms 34, and seated in the shallow groove 35. When bleeding occurs and an occluder pin 10 is required to be implanted, the applicator 12 with a pin 10 retained in it can readily be adjusted in configurations by bending of the shaft 28 and adjustment of the handle 30, immediately prior to insertion of the pin 10.

Figure 4:
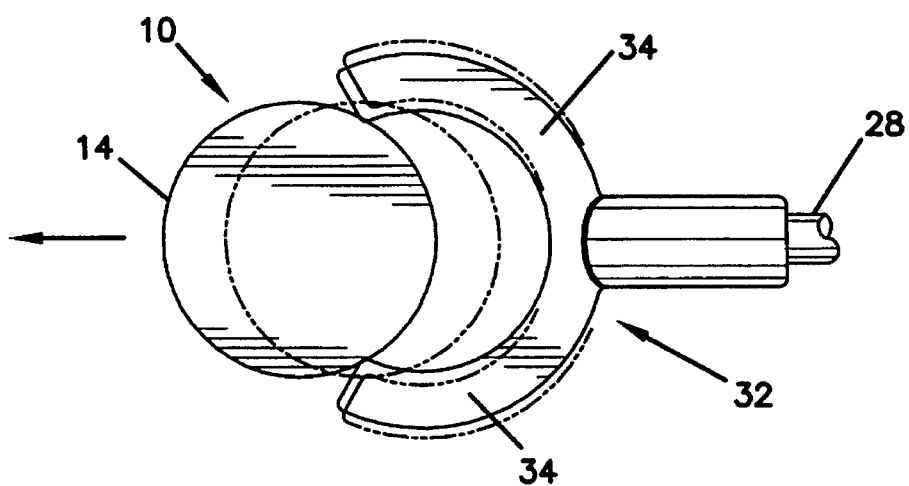
FIG. 4 is a top view of the yoke-type pin head holder of the applicator, showing in phantom how the arms of the pin holder are flexed laterally outward as the head of the pin is slid out from the arms.

As shown in FIGS. 1 and 4, the angle subtended by the arc formed by the arms 34 of the pin cap holder 32 is slightly more than 180°, and the diameter of the inner surface of the arms 34 is slightly smaller than the diameter of the outer periphery of the cap 14. Therefore, the cap 14 of the pin 10 is retained within the arms 34 after insertion through the opening between the ends of the arms 34. The yoke-type holder 32 is made of flexible plastic which provides some resiliency, and the small interior groove 35 holds the pin 10 in proper orientation. As shown in FIG. 4, the pin cap 14 can thus be slid laterally from the holder 32, parallel to the plane of the cap 14, with the arms 34 of the yoke flexing out slightly, thereby allowing the cap and the pin 10 to be freed. In addition, the pin 10 may in some circumstances need to be freed by being pushed perpendicularly to the plane of the arms 34, and this can also be done, although greater force is required. Thus the pin 10 can be separated from the pin holder 32 in either a lateral or perpendicular direction as may be required by the particular circumstances of the surgery. The arms 34 are stiff enough to retain the pin 10 until pressure is applied. Yet the pin holder 32 is flexible enough so that only slight force is required to flex the arms 34 outward so that the pin cap 14 can be slid from the holder 32.

Figure 6:
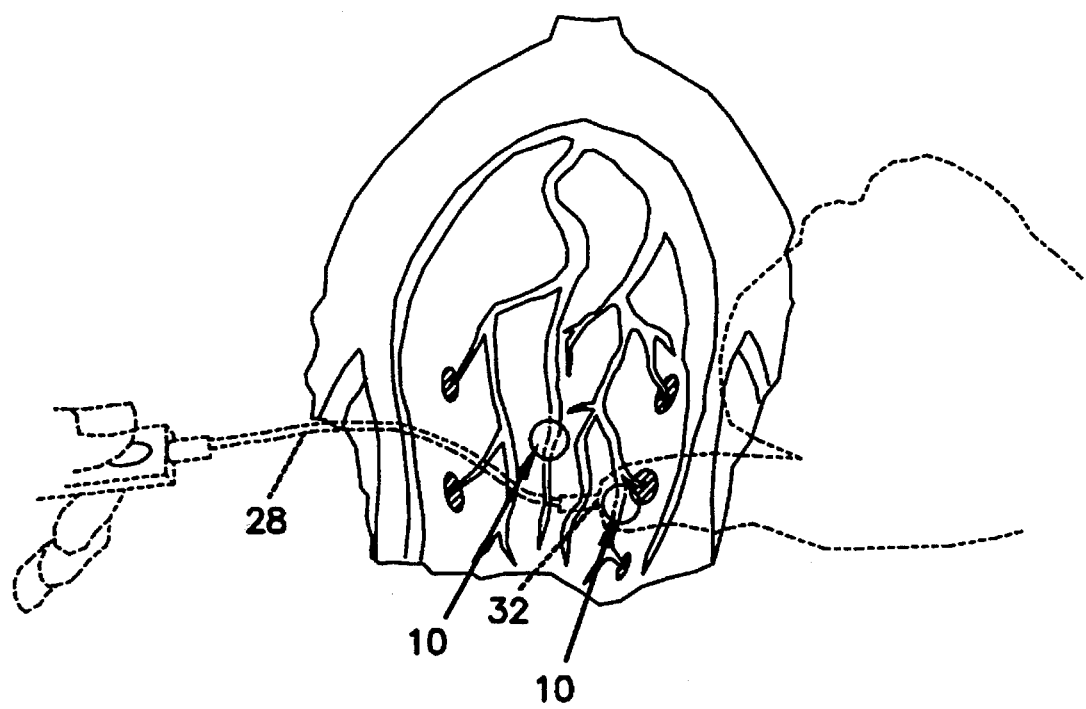
FIG. 6 is a perspective representation as to how pins are implanted by a surgeon to occlude presacral bleeding in colorectal surgery.

In use, the applicator 12 and pin 10 are readied by placing the pin 10 in the pin holder 32 so that it is retained by the arms 34, as shown in FIG. 1. Before bleeding occurs and the need arises for using an occluder pin 10, the applicator 12 and pin 10 combination can be placed along with other surgical tools for easy accessibility. The applicator 12 is then formed into a shape that provides free access of the occluder pin to the bleeding site. This is done by bending and twisting the shaft 28 so that the handle 30 is in a position desired by the surgeon, with the shaft 28 being spaced from surrounding tissue, and with the occluder pin 10 being juxtaposed properly with respect to the bleeding site and the sacrum. As seen in FIG. 6 the surgeon grips the applicator 12 in one hand at the handle 30 so that the pin 10 is positioned above the insertion point with the shaft 16 perpendicular to the sacral vertebrae. With the thumb or a finger of his free hand, the surgeon pushes the pin 10 into the bony cortex so that the bleeding vessel is occluded by the pin cap 14. The leading edges 20 at the serrations 18 spaced along the pin shaft 16 engage the surrounding region to secure the occluder pin 10 in the cartilage and prevent displacement.

It can be appreciated that although the pin 10 can be pushed perpendicularly to the plane of the arms 34 the pin holder 32 will usually be slid laterally from the pin, as shown in FIG. 4. The method of removal of the pin 10 from the applicator 12 is, however, dictated by the conditions of the operation. If the bleeding site is small and the pin 10 has been precisely inserted, the pin shaft 16 alone will stop the hemorrhaging. Otherwise, the head 14 tamponades the vein so that bleeding is quickly stopped. The edges 20 on the shaft then act similarly to barbs and resist withdrawal from the surrounding bony cortex so that the occluder pin 10 remains in place. Since the pin 10 is made of titanium or other non-reactive material, the pin 10 may be left in place without fear of displacing or causing a physical reaction to the pin material.

Figure 7:
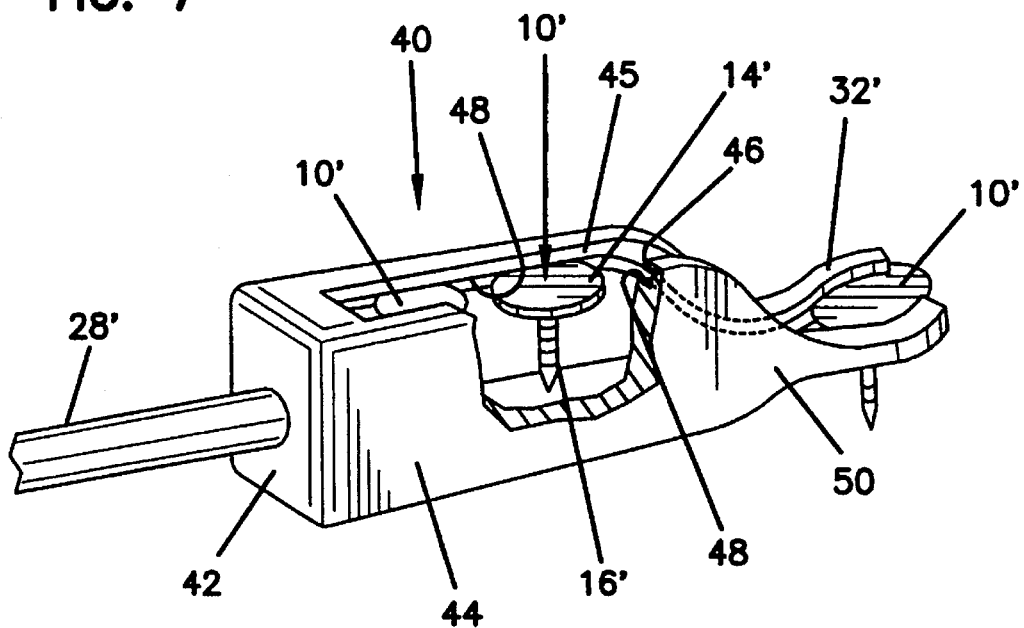
FIG. 7 is an enlarged perspective view, partially in section, of a portion of an applicator showing a variant for retaining and using several pins.

The example of FIG. 7 shows only a multi-pin holder 40 and only the end of a malleable extender shaft 28', the holder 40 including a base 42 which is attached to the shaft 28' in fixed or frictionally rotatable fashion. A channel 44 of generally U-shaped configuration extends forwardly from the base 42, the two side walls of the channel having lateral upper flanges 45, 46 with interior grooves 48 spaced apart to hold the caps 14' of pins 10' in slidable relation. The shafts 16' of the pins 10' extend down into the channel 44 but the sharp tips are enclosed by the bottom wall of the channel 44. The interior grooves 48 curve downwardly within a forwardly extending neck portion 50 that leads to a terminating C-shaped yoke-tip pin cap holder 32' as shown in FIGS. 1–4. Small detents (not shown) may be used along the grooves 48 to hold the pins 10' in position in the channel 44 until they are to be moved from the reserve locations to the active position between the arms 34', for implantation during surgery.

With this type of holder 40, the surgeon can have at least one additional pin 10' in reserve, which he can implant simply by pushing the cap 14' forwardly through the neck portion to the arms 34'. Although the channel 44 as shown is of a length sufficient to hold two pins 10' in reserve, it could alternatively hold only a single one or be long enough to hold three or more. The fact that the reserve pins 10' are adjacent and immediately accessible can substantially speed the operative proceeding and reduce the effects of inadvertently occurring bleeding sites.

Figure 8:
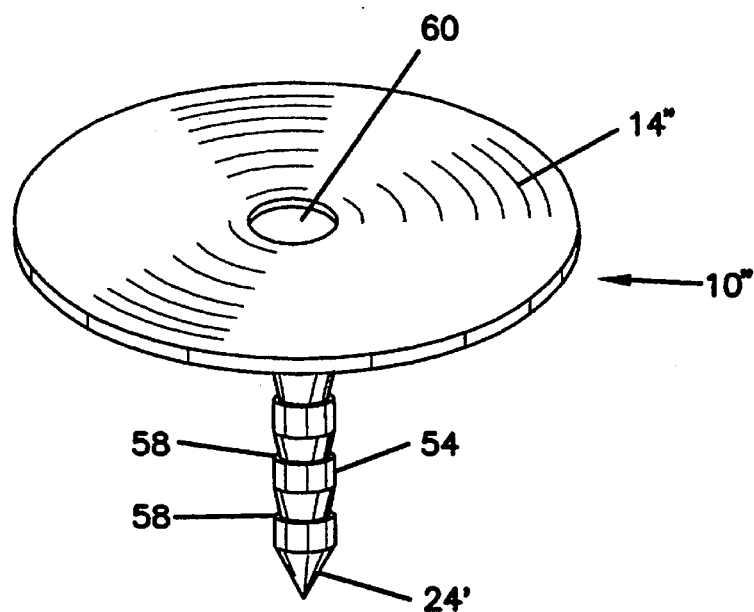
FIG. 8 is a perspective view of a modified occluder pin having a tapered shaft and an indented cap.
Figure 9:
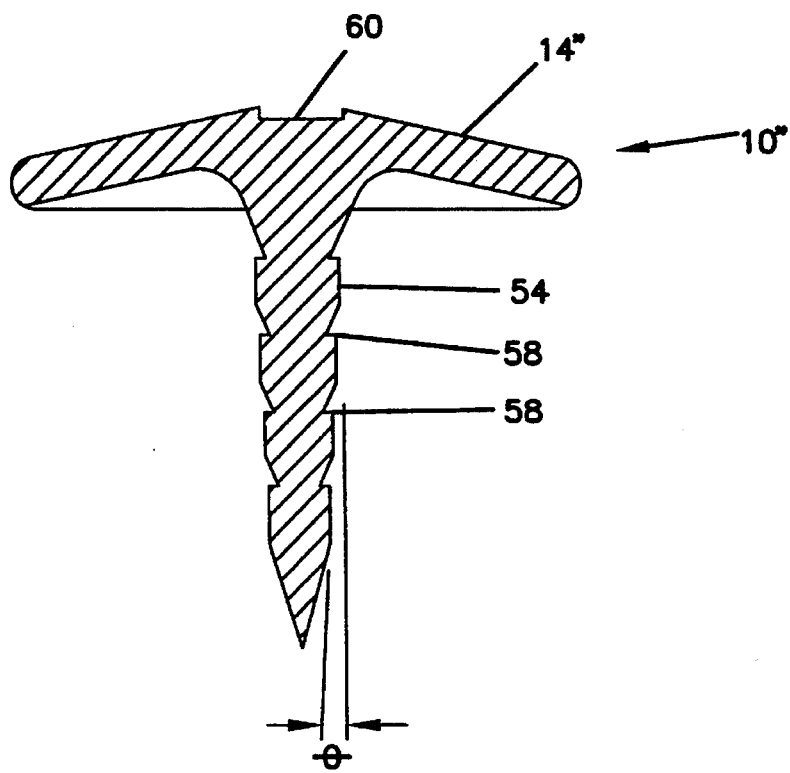
FIG. 9 is a cross-sectional view of the occluder pin of FIG. 8.

A modified occluder pin as shown in FIGS. 8 and 9 incorporates a number of features which can individually be used in the example of FIGS. 1—3. Here the occluder pin 10" has a slightly tapered shaft 54, the taper being at an angle e of less than about 2° (here about 1.39°) relative to the longitudinal axis of the shaft 54. In this example the taper reduces the shaft 54 diameter from 1.53 mm adjacent the head end to 1.27 mm adjacent the pointed tip, over a length of about 6.26 mm. The taper facilitates entry into the bony cortex and reduces the amount of force necessary, which can be important in some circumstances. The cap 14" angles radially downward slightly from its central region and has a diameter of about 9.52 mm, while the length of the pin is about 8.98 mm total. A leading edge 58 in the serrations enhances the barb-like action to hold the occluder pin 10" in place and oppose tendencies of the shaft 54 to work itself out. Although the angle of the leading edge transition is shown as 90° relative to the longitudinal axis of the shaft, the leading edge can also be undercut slightly to enhance the holding action. In addition, the cap 14" of the occluder pin 10" has a central indentation 60 on its superior surface, against which the tip of a mechanical member (not shown) may be placed. This indentation 60 is useful in one of a number of ways. When the occluder pin 10" has been partially inserted the surgeon or an assistant may use a long punch-type tool to urge or lightly tap the occluder pin into final position in the bony cortex. Alternatively a mechanical leverage tool may be used for this purpose. The holder may be kept in place during part or all of this procedure.

It is to be understood, however, that even though numerous characteristics and advantages of the present invention have been set forth in the foregoing description, together with details of the structure and function of the invention, the disclosure is illustrative only, and changes may be made in detail, especially in matters of shape, size and arrangement of parts within the principles of the invention to the full extent indicated by the broad general meaning of the terms in which the appended claims are expressed.

What is claimed is:

1. An applicator for use by a surgeon in applying an occluder pin having a cap to terminate sacral hemorrhaging comprising:

a handle elongated along a selected axis, a malleable thin metal extender shaft attached to the handle and nominally positioned along the selected axis, the extender being manually deformable both along and about its length and without a memory characteristic such as to retain its shape when deformed to a shape desired for proximity to a location at which sacral hemorrhaging is occurring; and a C-shaped pin cap holding member attached to the opposite end of the extender from the handle, the pin cap holding member having elastically deformable arcuate arms defining a curved periphery, the curved periphery including a recessed surface formed of a continuous groove extending substantially along the distance of the curved periphery for receiving and retaining the occluder pin cap in a releasable engagement, wherein the arcuate arms define a plane parallel to the axis of the handle at the said opposite end from the handle, and the arcuate arms terminate at spaced apart ends to define a gap, such that upon pressure applied to the occluder pin cap, the pin cap moves between the arcuate arms of the pin cap holding member or upon applying pressure to the occluder pin cap by raising the pin cap holding member in a perpendicular direction to the occluder pin, the arcuate arms elastically deform such that the pin cap is slidably separated from the pin cap holding member.

2. An applicator for use by a surgeon in applying an occluder pin having a cap to terminate sacral hemorrhaging comprising:

a handle elongated along a selected axis, a malleable thin metal extender shaft attached to the handle and nominally positioned along the selected axis, the extender shaft being manually deformable and without a memory characteristic, to retain its shape after deformation; and a pin cap holding member attached to the opposite end of the extender from the handle and having arcuate arms for receiving the occluder pin, wherein the arcuate arms form a plane parallel to the selected axis of the handle and wherein the handle is rotatably attached to the extender shaft so that the handle can be turned about the selected axis against frictional restraint.

3. An applicator as set forth in claim 2 above, wherein the pin cap holding member comprises a pair of arcuate arms extending around more than half of the circumference of the pin head and including an interior groove for receiving the periphery of the pin.

4. An applicator as set forth in claim 3 above, wherein the arms are flexible such that the pin cap may pass between the arms so that the arms flex outward slightly.

5. An applicator as set forth in claim 2 above, wherein the holding member includes means disposed between the holding member and the extender shaft for retaining at least one occluder pin in a reserve position.

6. An applicator as set forth in claim 5 above, wherein the means for retaining comprises means defining an open-topped channel having interior side grooves for receiving the cap of at least one occluder pin in slidable relation, and an arcuate neck portion including interior side grooves for retaining an occluder pin movable from the channel to the holding member, the channel including a wall concealing the tip of the reserve occluder pin.

7. An applicator for use by a surgeon in applying an occluder pin to terminate sacral hemorrhaging comprising:

a handle elongated along a selected axis, a malleable thin metal extender shaft attached to the handle and nominally positioned along the selected axis, the extender being manually deformable and without a memory characteristic such as to retain its shape; and a pin cap holding member attached to the opposite end of the extender from the handle, wherein the holding member includes means disposed between the holding member and the extender shaft for retaining at least one occluder pin in a reserve position, the means for retaining having a means defining an open-top channel having interior side grooves for receiving the cap of at least one occluder pin in slidable relation and an arcuate neck portion including interior side grooves for retaining an occluder pin moveable from the channel to the holding member, the channel including a wall concealing the tip of the reserve occluder pin.

8. An applicator for use by a surgeon in applying an occluder pin having a cap to terminate sacral hemorrhaging comprising:

a handle extended along a selected axis;

a malleable thin metal extender shaft attached to the handle, the extender shaft being manually deformable along the selected axis to align with a secondary axis at its distal end, the extender shaft being without a memory characteristic, to retain its shape after deformation; and an elastically deformable pin cap holding member attached to the opposite, distal end of the extender shaft from the handle and having arcuate arms including a continuous groove, the groove forming a recessed surface along substantially the internal perimeter of the arcuate arms for receiving the occluder pin cap in a sliding relation, the arcuate arms forming a plane nominally parallel to the axis of the extender shaft at its distal end and defining an open gap between the ends of the arms, wherein the holding member retains the sides of the occluder pin cap positioned along the secondary axis with the top of the occluder pin cap being accessible for the application of force to slidably disengage the pin from the retaining surface by moving the holding member laterally with respect to the occluder pin cap through the open gap between the ends of the arms for insertion of the pin.

* * * * *